United States Patent [19]

Sarkki et al.

[11] 4,448,790
[45] May 15, 1984

[54] PROCESS FOR FRACTIONING GRAIN FLOUR INTO COMPONENTS OF FOOD QUALITY

[75] Inventors: Marja-Leena Sarkki, Naantali; Martti Söderström, Turku; Hannu Maunula, Turku; Annika Korhonen, Turku, all of Finland

[73] Assignee: Oy Vehnä AB, Raisio, Finland

[21] Appl. No.: 340,646

[22] Filed: Jan. 19, 1982

[30] Foreign Application Priority Data

Jan. 28, 1981 [FI]  Finland ................................ 810246

[51] Int. Cl.$^3$ ..................... A23J 1/12; A23L 1/195; A23L 1/09
[52] U.S. Cl. ..................................... 426/52; 426/18; 426/622; 435/99; 260/112 G; 127/56
[58] Field of Search ................. 426/52, 49, 622, 18, 426/20, 21; 435/96, 99

[56] References Cited

U.S. PATENT DOCUMENTS

| | | | |
|---|---|---|---|
| 3,249,512 | 5/1966 | Bode | 435/96 |
| 3,291,702 | 12/1966 | Miescher | 435/96 |
| 3,329,578 | 7/1967 | Faucett et al. | 435/96 |
| 3,806,415 | 4/1974 | Hayes | 435/96 |
| 3,849,194 | 11/1974 | Armbruster et al. | 435/99 |
| 3,922,198 | 11/1975 | Kuske et al. | 435/96 |
| 3,962,465 | 6/1976 | Richter et al. | 435/99 |
| 4,154,623 | 5/1979 | Schwengers et al. | 127/67 |
| 4,217,414 | 8/1980 | Walon | 435/99 |
| 4,311,714 | 1/1982 | Goering et al. | 426/52 |

*Primary Examiner*—Raymond N. Jones
*Assistant Examiner*—Marianne S. Minnick
*Attorney, Agent, or Firm*—Wolf, Greenfield & Sacks

[57] ABSTRACT

The present invention is concerned with a process by means of which the fraction of grain flour that remains after separation of the main part of the starch and of the gluten-type protein, when the grain contains gluten, is divided into two products of food quality. One of these products consists mainly of the albumin-globulin-type, water soluble proteins and the other one, a syrupy product, consists mainly of sugars obtained as products of hydrolysis of small-particle starch of grain. The homogenous slurry obtained after separation of ordinary grain starch and gluten from the grain flour by known methods is heated at a temperature of at least 120° C., treated at a temperature of at the most 90° C. simultaneously by means of alpha-amylase and beta-glucanase, the produced protein precipitate is separated from the sludge, washed, and dried. The remaining clear fraction is sugared by means of amyloglucosidase of fungalamylase.

10 Claims, 1 Drawing Figure

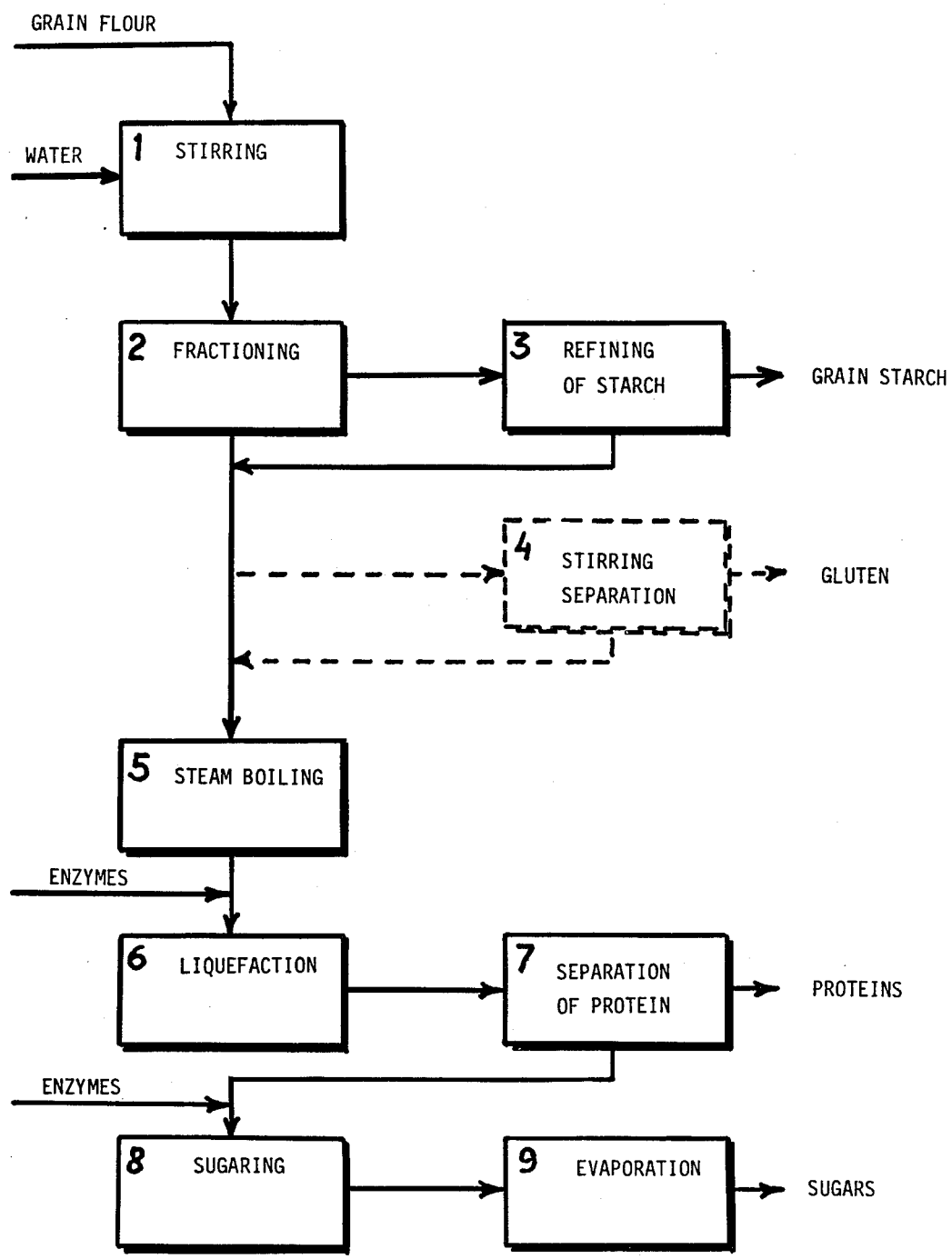

PROCESS FOR FRACTIONING GRAIN FLOUR INTO COMPONENTS OF FOOD QUALITY

The present invention is concerned with a process by means of which the fraction of grain flour that remains after separation of the main part of the starch in the grain flour, and possibly of the gluten-type protein, which remaining fraction contains 15 to 40 percent by weight of the dry substance of the grain flour, depending on the species of grain, is divided into two products of food quality, one of these products comprising a 20 to 35 percent-by-weight fraction of the dry substance, consisting mainly of the albumin-globulin-type proteins soluble in water of the grain, and the other one, a syrupy product, consisting mainly of sugars obtained as products of hydrolysis of small-particle starch of grain. By means of the process, grain flour can be fractioned into three, in the case of certain flour species, four, industrially usable products, which are ordinary grain starch, gluten in the case of certain grains species, syrup obtained from small-particle starch, and soluble proteins, so that no waste or waste waters are produced at all. Herein, grain flour is to be understood as meaning flours of grain species used for food purposes, such as wheat, rye, and barley, which have been ground in known ways and from which the husks have been removed, and ordinary grain starch is to be understood as meaning the large-particle main fraction of starch, which is peculiar of each grain species and which is relatively well separable. Below, the percentage numbers given refer to percentages by weight.

When ordinary grain starch and gluten are separated from grain flour, a fraction remains which contains the small-particle starch of the grain, whose particle size is 2 to 10 $\mu$m, the water-soluble albumin-globulin-type proteins of the grain, the main part of the hemicellulose and pentosans, as well as the main part of the mineral substances. The magnitude of the said fraction is 15 to 40 percent of the dry substance of the flour, depending on the species of grain. Until now, it has been impossible to separate the small-particle starch of grain from the other components of the fraction in a usable form in an economically meaningful way, because the surface of the small starch particles is covered by a thin network of protein, which protects the particles efficiently, e.g., from the effect of enzymes that hydrolyse starch. After separation of starch and washing, ordinary grain starch, whose particle size is 15 to 35 $\mu$m, contains 0.05 to 0.2% of protein, whereas small-particle starches contain 1.5 to 1.7% of protein as enriched on the surfaces of the particles. Also, soluble and insoluble pentosans, of which the latter ones are frequently called hemicellulose, are partly bound to small-particle starch, partly to proteins. Small-particle starch also differs from ordinary grain starch in the respect that it has a clearly higher gelatinizing or jellifying temperature as compared with corresponding ordinary grain starch.

In prior art, one knows enzymatic or acid hydrolysis of protein-containing starches obtained from grain and brought into an appropriate particle size by means of wet-grinding. Thus, according to the British Pat. GB No. 1,495,220, the fibres and the insoluble protein are removed by screening or centrifuging, whereupon the soluble protein is separated by ultrafiltration, and the glucose obtained by means of hydrolysis of starch is purified and dried. Alternatively, the glucose may be partly isomerized into fructose. The enzymatic hydrolysis is carried out by means of alpha-amylase at 70° to 80° C., pH 7.0, in 1 to 2 hours, and the liquid sugar obtained is converted into glucose by means of amyloglucosidase in a conventional way at 50° to 60° C., pH 3.5 to 4.0, in 10 to 72 hours.

According to the U.S. Pat. No. 4,154,623, it is known to wet-grind the grain and to remove the pentosan material, which is detrimental to enzymatic hydrolysis of starch, from the system together with grain husks as attached to the husks. In the process, the starch sludge, which is obtained by removing the fibres and husks, the insoluble pentosans, the germs, and the gluten, is heated at 80° to 120° C. and the starch is then liquefied by means of alpha-amylase at 85° C. The liquid sugar obtained is sugared enzymatically at 60° C., pH 4.8, in about 72 hours. The insoluble gluten is then removed by centrifuging, and the soluble protein by ultrafiltration.

From the German patent publication DE-OS No. 27 48 750, one knows suspending of wheat flour in water, separation of ordinary wheat starch by centrifuging and separation of wheat gluten from the starch of the protein fraction so that, before separation of gluten, the fraction is treated by means of bacterium-alpha-amylase at 45° to 60° C., pH 5 to 7, for no more than 6 hours. In the supplementary patent publication DE-OS No. 28 16 326, the said fraction is treated at 60° to 80° C. for less than 30 minutes, whereby at least 50% of the starch in the fraction is dissolved without being gelatinized, and the gluten of the wheat is separated as undenatured ('vital'). In the process, besides the ordinary starch, only the gluten is separated from the wheat flour, and even this as rather impure (66% of protein); on the contrary, the albumin-globulin-type soluble proteins of wheat remain in the solution. At the same time, it is ascertained that the higher temperatures and the longer period of treatment result in denaturation and considerable solubility of the gluten, whereby the sugared starch would contain a considerable quantity of dissolved gluten.

From the Japanese patent publication JP No. 52 033353 it is known to treat starch-containing waste waters with a glucoamylase enzyme fixed to a carrier, before the waste water is treated in a conventional way by means of an active sludge in a waste-water treatment plant.

From the British Pat. GB No. 1,244,288, it is known to prepare a protein composition suitable for foodstuff out of a starch-containing crude gluten obtained by wet-grinding of Indian corn or sorghum kernels. In the process, the starch-containing crude gluten is treated in a water sludge with alpha-amylase so as to hydrolyse the starch, and the sludge is then heated so as to destroy the enzyme at no less than 95° C. for at least 15 minutes, or at 100° to 150° C. for about one hour. The objective of the process is to purify gluten preparations separated by means of a prior-art wet-grinding process, in order to increase their protein content and to eliminate undesirable flavour and odour agents.

The European Pat. EP No. 0,001,470 describes a process for the treatment of the waste waters of a wheat-starch factory, and its objective is to facilitate the concentration of the waste water, because, without treatment, the sludge tends to foam when evaporated, its viscosity increases extensively, and protein and starch agglomerations are formed in the evaporator. The waste water is treated in an arbitrary sequence at least by means of heat treatment at 60° to 110° C., whereupon the solid material is separated off, and by means of enzymatic treatment, wherein the enzymes used are alpha-amylase and/or cellulase and/or hemicellulase, and, optionally, glucoamylase and/or beta-glucanase. The waste water to be treated contains 1.5 to 4% of dry substance, and it can be concentrated to a dry-substance content of 8 to 10%. The treatment with alpha-amylase and with cellulase or hemicellulase can be performed simultaneously at 60° to 80° C. and at pH 5 to 6. In the cases in which the protein-containing solid material is separated off, solutions are obtained that, besides sugars, also contain a considerable quantity of protein (about 19% of the dry substance). This is natural, because in the process no attention is paid to a maximum separation of the soluble proteins of wheat from the starch hydrolysates.

Thus, the prior-art processes are usually concerned with a specific grain species or with a similar group. In the processes, the emphasis is usually on a maximum purification of one fraction of material, so that a gluten or maximum purity or a starch or hydrolysate of starch of maximum purity is prepared. In the most efficient processes, three fractions are obtained, starch, gluten, and hydrolysate of starch, the first two of them being obtained as relatively pure, but the hydrolysate of starch always containing numerous impurities. If attempts are made to separate the soluble proteins of grain as a fraction of their own, this takes place by means of ultra-filtration or a corresponding costly and complicated process.

Now it has been noticed that it has been possible to develop a process by means of which the following advantages are obtained simultaneously:

it can be applied to all species of grain used for food purposes, by means of that process, the soluble proteins of grain can also be separated as a fraction of their own in an easy and economically favourable way, the hydrolysate of small-particle starch obtained contains only little protein as an impurity, with species of grain that form gluten, two protein fractions are obtained, which are the insoluble gluten as undenatured and very pure, in the case of wheat containing at least 80% of protein out of the dry substance, and the soluble albumin-globulin-type proteins as a fraction of their own, and no waste waters are produced in the process.

The process that has been developed will be described below with the aid of the attached graph. The ordinary grain starch and, especially in the case of wheat but also in the case of rye, the gluten, separated as agglomerations resembling dough, are separated in an arbitrary way out of the water sludge of ground grain (1) so that the flour sludge is fractioned (2), e.g., by centrifuging into a heavier starch fraction and a lighter fraction containing the proteins and the other components of the grain, and the ordinary grain starch contained in the heavy fraction and having a particle size of 15 to 35 μm, depending on the species of grain, is washed (3) and dried. Out of the light fraction, in the case of certain species of grain, such as wheat and rye, the dough-like gluten agglomerations formed during the process are separated by adding water, mixing, and centrifuging (4). Other species of grain do, as a rule, not form similar gluten agglomerations. The remaining homogeneous sludge, which, depending on the species of grain, contains 15 to 40% of the dry substance of the flour, contains the small-particle starch of the grain, whose particle size is 2 to 10 μm and whose particles are covered by a thin protein network, whose material quantity is 1.5 to 1.7% of the dry substance of the starch particle. Moreover, the sludge contains the proteins of the grain that are soluble in water or readily dispersed in water, the soluble and insoluble pentosans, partly bound to the soluble or dispersed protein material, and the main part of the mineral substances of the grain.

Now it has been noticed that the said homogeneous sludge can, according to the invention, be fractioned in a simple and economically meaningful way into two products of food quality so that the entire fraction is taken advantage of and that no waste waters or any other waste are produced. One of the products obtained, which contains 20 to 35% of the dry substance of the fraction to be treated, contains the protein of the fraction, the share of the protein in the dry substance of the product being at least 40%. It is characteristic of the said protein product that its ability to bind water is 300 to 450%, in other words, one unit of weight of dry product is capable of binding at least three units of weight of water. The other one of the products obtained contains the main part of the small-particle starch and of the pentosans of the grain as dissolved syrupy liquid sugar, which contains no more than 4% of protein, as calculated from the dry substance of the syrup.

According to the invention, the homogeneous sludge, which has been obtained from the water sludge (1) of the grain flour by from it separating the ordinary grain starch and, if necessary, the gluten, is heated, e.g., in a steam boiler by means of direct steam (5) at 120° to 160° C. for 1 to 10 seconds, whereby the protein network on the surface of the particles of the small-particle starch is split and the starch is gelatinized. At the same time, the soluble or finely dispersed protein contained in the sludge is denatured and starts forming a readily separable precipitate. The sludge is now cooled at 70° to 90° C., and 0.1 to 0.5% of alpha-amylase and 0.1 to 1.0% of beta-glucanase are added to it, as calculated from the dry substance of the sludge. The enzymes are allowed to influence simultaneously for 0.5 to 2 hours, during which period the starch and the pentosans are hydrolysed and form readily soluble oligosaccharides (6). At the same time, about 20 to 35% of the dry substance of the sludge is precipitated as a protein precipitate, which contains protein as a quantity of 40 to 60% of the dry substance of the precipitate.

The protein precipitate is separated from the dissolved materials, e.g., by centrifuging (7), washed briefly if necessary, and dried. The remaining clear syrupy liquid is sugared (8) at 50° to 55° C. over 20 to 40 hours by using amyloglucosidase or fungalamylase as a quantity of 0.1 to 0.5% of the dry substance of the liquid until the dextrose equivalent (DE) illustrating the sugar content is 20 to 80. If necessary, the sugar liquid obtained can be evaporated (9) into syrup whose dry-substance content is 55 to 75%. The syrup contains glucose, maltose, pentoses, and lower oligosaccharides, and, moreover, it contains a maximum of 4% of protein substances, as calculated from the dry substance of the syrup.

Like the protein product obtained, the syrup may also be used as a nutrient and/or functional additive in the manufacture of foodstuffs.

The invention will still be illustrated by means of the following examples, which represent different embodiments of the invention without, nevertheless, restricting the scope of the invention:

EXAMPLE 1

Wheat flour that was ground in the ordinary way as dry was mixed into a 1.5-fold quantity of water to form a homogeneous sludge, which was fractioned by centrifuging into a heavier fraction and a lighter fraction. The heavier fraction, which contained the ordinary wheat starch, of an average particle size of 25 to 35 $\mu$m, was washed briefly and dried in the ordinary way. The lighter fraction was stirred slowly at 45° C. until visible gluten "mycelia" started being formed (about 0.5 h), whereupon water was added and the mix was stirred strongly. The separated gluten agglomerations were washed briefly and dried in the ordinary way. The gluten contained protein as a quantity of 80.5% of the dry substance.

The fraction remaining after the separation of the gluten contained 15% of dry substance. It was heated in a steam boiler by means of direct steam at 160° C. for 2 seconds and was then cooled to 85° C. To the sludge, 0.2% of Thermamyl 60 L amylase (Novo, 60 KNU/g) and 0.1% of beta-glucanase (ABM, 750 D/g) were added, as calculated from the dry substance of the sludge. The enzymes were allowed to influence for one hour, during which time a clear protein precipitate was formed. The precipitate was removed by means of a continuous centrifuge and dried. The precipitate contained 24% of the dry substance of the fraction, and it contained 58% of protein, as calculated from the dry substance.

The remaining clear starch hydrolysate was treated for 36 hours at 50° C. by means of 0.2% of amyloglucosidase (Novo, 150 AGU/ml), whereby the dextrose equivalent (DE) of the syrup obtained was 75. The syrup was evaporated to a dry-substance content of 75%.

EXAMPLE 2

The fraction obtained in accordance with Example 1 after removal of gluten was heated in a steam boiler at different temperatures for 4 seconds and then treated with alpha-amylase and beta-glucanase in accordance with Example 1. The protein precipitates obtained were separated by means of a centrifuge and dried, whereby the following yields and protein contents were obtained:

| heating temperature °C. | protein product | |
|---|---|---|
| | yield % from dry substance of fraction | protein content % from dry substance of product |
| 100 | 48 | 23 |
| 115 | 44 | 25 |
| 135 | 31 | 45 |
| 140 | 24 | 50 |
| 170 | 18 | 60 |

EXAMPLE 3

After separation of the gluten agglomerations, the light fraction prepared in accordance with Example 1 contained 15.7% of dry substance, and the particle size of the starch contained therein was 2 to 10 $\mu$m. The fraction was heated in a steam boiler, in accordance with Example 1, to 160° C. and cooled then to 90° C., at which temperature the sludge was treated with 0.4% of Thermamyl enzyme over 1 hour. The precipitated protein product contained 45% of the dry substance of the fraction, and its protein content was 25% of the dry substance of the product. When the sludge obtained was, after an alpha-amylase treatment, treated at 70° C. with 0.7% of beta-glucanase, after a treatment of 1 hour, 30% of the dry substance of the fraction was obtained as a protein product whose protein content was 52%.

The syrup obtained after separation of the protein product was sugared by using 0.5% of amyloglucosidase, as calculated from the dry substance of the syrup, at 50° C. over different periods of time, whereby the following dextrose equivalents were obtained:

| t (h) | 0 | 8 | 12 | 30 | 40 |
|---|---|---|---|---|---|
| DE | 18 | 60 | 66 | 71 | 75 |

EXAMPLE 4

When rye flour was fractioned in the way described in Example 1, initially the ordinary rye starch was separated, whose particle size was 25 to 30 $\mu$m. After the protein precipitate produced during the process has been removed, the remaining homogeneous sludge contained the small-particle starch, particle size 3 to 10 $\mu$m, and, in addition to that, the soluble and dispersed protein, as well as hemicellulose. The dry-substance content of the fraction was 21%. The fraction was heated in a steam boiler for 5 seconds at different temperatures, and after heating, the sludge was cooled to 80° C. and treated over 2 h with 0.3% of Thermamyl amylase and with 0.5% of beta-glucanase, as calculated from the dry substance. The protein precipitates were removed by centrifuging, whereby, at different heating temperatures, the following protein contents of the protein products were obtained:

| heating temperature °C. | protein content of protein product % from dry substance of product |
|---|---|
| 100 | 21 |
| 120 | 40 |
| 140 | 45 |
| 160 | 56 |

The syrup obtained after separation of the protein product was sugared by means of 0.22% of amyloglucosidase at 50° C. over different periods of time, whereby the following sugaring degrees were obtained:

| t (h) | 0 | 8 | 12 | 30 | 40 |
|---|---|---|---|---|---|
| DE | 19 | 40 | 65 | 70 | 75 |

EXAMPLE 5

Barley was fractioned so that it was wet-ground in a conventional way, the husk parts were removed by screening, and the starch, whose particle size was 15 to 30 $\mu$m, was separated by centrifuging. The remaining fraction contained the small-particle starch, of an average particle size less than 2 $\mu$m, the dissolved and dispersed protein, the hemicellulose, and the mineral substances.

0.5% of Thermamyl enzyme was added to the fraction, and the fraction, whose dry-substance content was 10%, was heated in a steam boiler for 8 seconds at 120°

C., cooled to 80° C., and 1.0% of beta-glucanase was still added to it. The enzymes were allowed to act for 2 hours. The sludge was now cooled to 50° C., and 0.5% of fungal-amylase named Fungamyl 800 L (Novo, 800 FAU/g) was added to it. The sugaring time was 36 h, whereupon the protein that was precipitated in the cooking and that was not dissolved was separated by centrifuging, as a protein product containing 42% of protein, as calculated from the dry substance of the product. The remaining starch syrup contained mostly maltose, and its dextrose equivalent was 40.

EXAMPLE 6

Barley flour was fractioned in the way described in Example 1, and the fraction containing small-particle starch, the dry-substance content of which fraction was 25% and which fraction contained 19% of protein, as calculated from the dry substance, was heated in a steam boiler at 160° C. for 10 seconds was cooled to 80° C. 0.4% of Thermamyl amylase and 0.8% of beta-glucanase were added to the fraction, and they were allowed to act for 1 hour. The precipitated and undissolved protein was separated by centrifuging; the yield was 32% out of the dry substance of the fraction, and the precipitate contained 60% of protein, as calculated from the dry substance of the precipitate. The remaining syrup was sugared by means of 0.2% of amyloglucosidase over 40 h at 50° C., and the solution was evaporated to a dry-substance content of 60%. The ultimate DE of the syrup was 77.

We claim:

1. A process for fractioning grain flour into at least three fractions of food quality including starch, protein and sugar fractions comprising:
   (a) slurrying the grain flour into water;
   (b) separating the resulting slurry into a heavier fraction containing ordinary grain starch having a particle size of about 15 to 35 mm and a lighter fraction containing about 15 to 40% of the dry substance of the flour containing protein covered small particle starch having a particle size of about 2 to 10 mm and a protein content of about 1.5 to 1.7% of the dry substance of the starch particle,
   (c) heating said lighter fraction from step (b) to a temperature of at least 120° C. for a period of time sufficient for the protein network on the surface of the particles of the small particle starch to split and the starch to be gelatinized,
   (d) cooling said lighter fraction from step (c) to a temperature of 90° C. or lower and treating said lighter fraction simultaneously with alpha-amylase and beta-glucanase;
   (e) separating the resulting protein precipitate from the lighter fraction from step (d) as a precipitate constituting about 20 to 35% of the dry substance of the lighter fraction and containing about 40 to 60% protein based on the dry substance of the precipitate to obtain a clear fraction remaining after separating the precipitate; and
   (f) saccharifying the clear fraction from step (e) with amyloglucosidase or fungal amylase at a temperature of 55° C. or lower until the dextrose equivalent is at least 20 to 80.

2. A process as in claim 1, wherein said lighter fraction is heated in step (c) to a temperature of between 120° C. and 160° C.

3. A process as in claim 1, wherein the enzyme treatment of step (d) takes place at a temperature of between 70° C. and 90° C. over a period of from 0.5 to 2 hours.

4. A process as in claim 1, wherein from 0.1 to 0.5% by weight of alpha-amylase and from 0.1 to 1.0% by weight of beta-glucanase are used as calculated from the dry substance of the fraction.

5. A process as in claim 1, wherein the clear fraction remaining after separation of the protein precipitate is saccharified in step (f) at a temperature of between 50° C. and 55° C. by using 0.1 to 0.5% by weight of amyloglucosidase or fungalamylase as calculated from the dry substance of the clear fraction.

6. A process as in any one of claims 1-5 wherein said process is performed in a completely sealed system having a water circulation means.

7. A process as in claim 1, wherein the separation of step (b) is performed by centrifugation.

8. A process as in claim 1, wherein the heavier fraction resulting from step (b) is washed and dried to yield ordinary grain starch.

9. A process as in claim 1 wherein, the grain contains gluten, the gluten is present in the lighter fraction and agglomerates between steps (b) and (c) and the agglomerates are removed by mixing said lighter fraction with water and filtering or centrifuging to separate the gluten agglomerates.

10. A process as in claim 1, further comprising the step of concentrating the sugar fraction resulting from step (f) by evaporation of water contained in said fraction.

* * * * *